United States Patent [19]

Hurley et al.

[11] Patent Number: 5,355,871
[45] Date of Patent: Oct. 18, 1994

[54] ELASTOMERIC CONTROLLER FOR ENDOSCOPIC SURGICAL INSTRUMENTS

[75] Inventors: Paul Hurley; James F. Caruso, both of Chicago, Ill.

[73] Assignee: Dexide, Inc., Fort Worth, Tex.

[21] Appl. No.: 943,514

[22] Filed: Sep. 11, 1992

[51] Int. Cl.⁵ .................. A61B 17/00; A61M 3/00
[52] U.S. Cl. ........................ 128/20; 604/159; 604/198; 604/212; 606/170; 606/205
[58] Field of Search ............ 128/3, 20; 604/158, 604/159, 163, 198, 212, 214, 107; 606/170, 198, 205, 106, 127

[56] References Cited

U.S. PATENT DOCUMENTS

| | | | |
|---|---|---|---|
| 3,276,632 | 10/1966 | Stanzel | 604/198 X |
| 3,840,008 | 10/1974 | Noiles | 604/158 X |
| 3,982,544 | 9/1976 | Dyck | 604/159 X |
| 5,211,652 | 5/1993 | Derbyshire | 606/206 X |
| 5,226,894 | 7/1993 | Haber et al. | 604/198 |
| 5,282,817 | 2/1994 | Hoogeboom et al. | 606/205 X |

FOREIGN PATENT DOCUMENTS

| | | | |
|---|---|---|---|
| 0317518 | 5/1989 | European Pat. Off. | 604/192 |
| 0265972 | 10/1913 | Fed. Rep. of Germany | 604/158 |
| 9220292 | 11/1992 | PCT Int'l Appl. | 606/170 |

Primary Examiner—Richard J. Apley
Assistant Examiner—Donna L. Maraglio

[57] ABSTRACT

A body controller is provided for an endoscopic surgical instrument having a cylindrical housing and an instrument body concentrically disposed interior of the housing and moveable between first and second positions. The controller is designed to accommodate and be activated by light grasping and, preferably, compressive application of, a finger or thumb of the human operator to a section which preferably includes a flexible dome-like or other similarly shaped portion which is substantially immediately responsive to the application of the hand of the surgeon or other operator to activate a surgical instrument carried within the housing, such as a retractable needle, or the like, to one position. By withdrawing the finger or thumb of the surgeon from the flexible means, the instrument body may be moved to a second, or original, position.

8 Claims, 2 Drawing Sheets

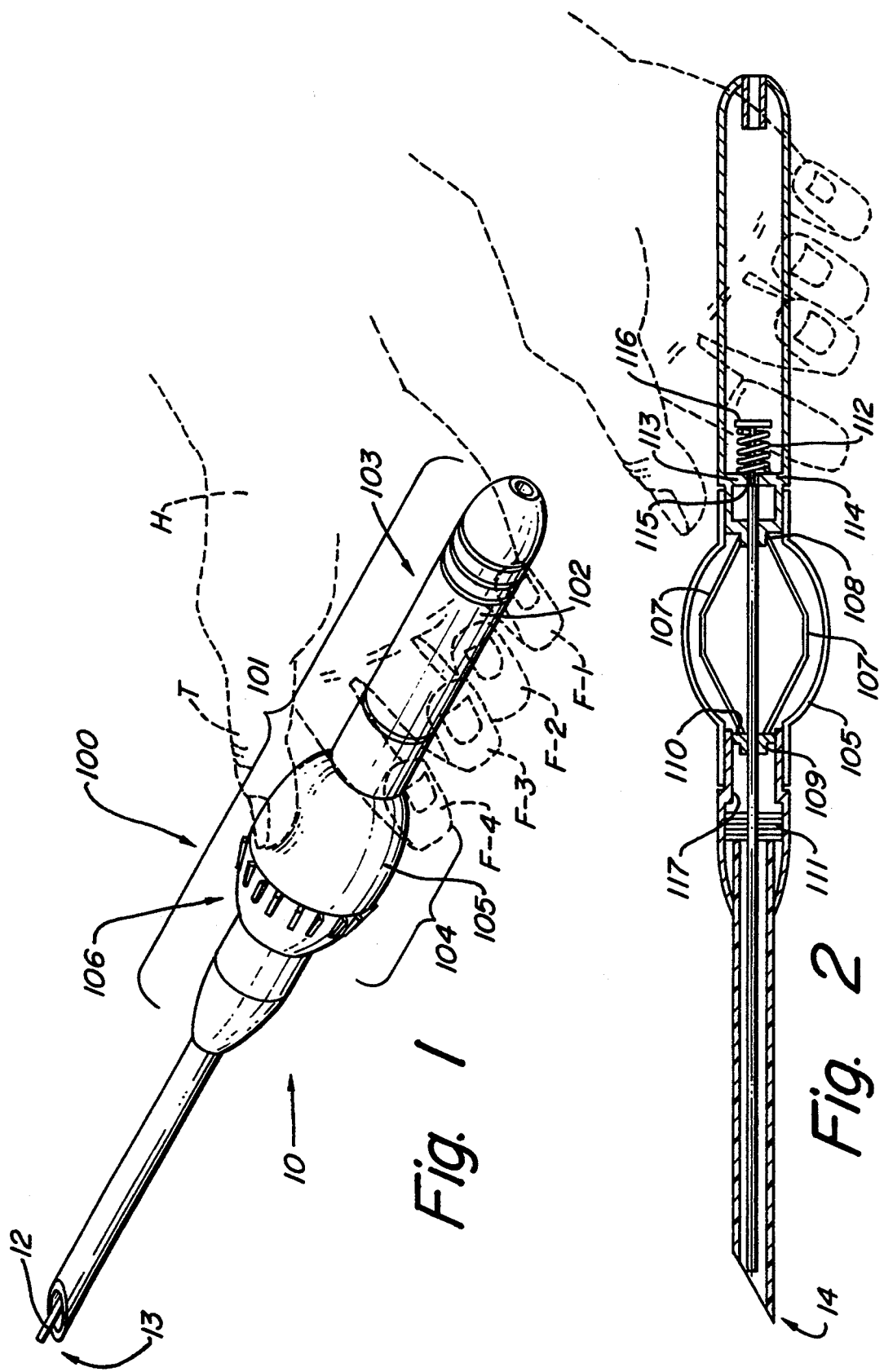

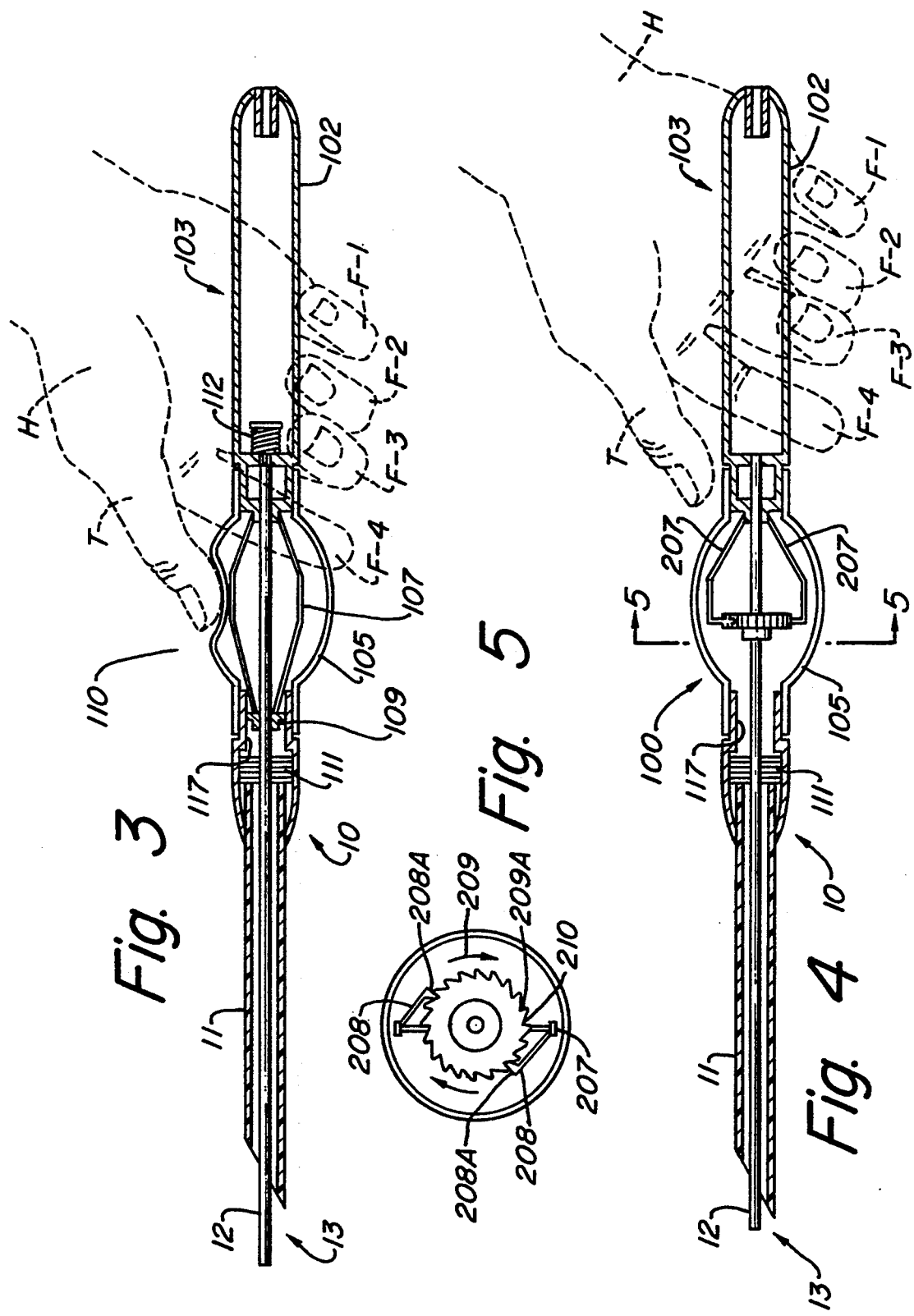

ELASTOMERIC CONTROLLER FOR ENDOSCOPIC SURGICAL INSTRUMENTS

BACKGROUND OF THE INVENTION (1) Field of the Invention:

The invention relates to a body controller for endoscopic surgical instruments.

(2) Brief Description of the Prior Art:

Surgical procedures require considerable touch and feel of the surgeon in the operation of the particular surgical instrumentation in order to satisfactorily and carefully accomplish the desired objective of the surgical procedure. Accordingly, surgical instruments must incorporate into their design and operability, the ability of the surgeon to rely on simple touch techniques for activation of the instruments.

Such objectives are particularly critical with respect to endoscopic surgical instruments. Endoscopic procedures gain access to the inside of an anatomical cavity by using an implement, such as a trocar, cannula, or a needle having a sharpened point, to pierce or puncture the bodily tissues, muscles, membranes, or the like, which may form a portion or surround the cavity wall. A surgical needle, for example, may be used to pierce a cavity or a blood vessel, subarachnoid heat ventricle, or the like. After piercing such cavity, the needle may be left in situ and used to inject or withdraw gases or liquid-phase fluids from the cavity, or to insufflate the cavity by injection of, for example, a particular inert gas or other fluid.

Since the area in which the surgeon must perform procedures incorporating endoscopic surgical instrumentation is smaller than that normally encountered when conventional surgical techniques are employed, reliance by the surgeon upon his touch and feel during the surgery becomes even more critical, and surgical instrumentation must take this factor into consideration such that touch and feel are transferred between the surgeon's hand and the fingers through the instrument and between the area of operation with the abdomen and the surgeon's hand.

The present invention addresses the problems and the deficiencies of the prior art, as generally discussed above.

SUMMARY OF THE INVENTION

The present invention provides a controller for endoscopic surgical instruments in which the instrument includes a cylindrical housing and an instrument body concentrically disposed interiorly of the housing and moveable therein between first and second positions. The body controller includes a hand-held housing which extends to the cylindrical housing and receives at least a part of the instrument body. The hand-held housing includes a first section preferably having a first outer diameter for gripping engagement by the fingers of a human operator, such as a surgeon. The housing includes a second section having a flexible element preferably with an outer diameter normally compressive in variation to the outer diameter of the first section. The control means are disposed within the cylindrical housing and operatively extend between the instrument body and the flexible element for directing movements of the instrument body. Control means are responsive to finger or thumb application of the flexible means to urge the control means in one direction to move the instrument body between first and second positions.

BRIEF DESCRIPTION OF THE DRAWINGS

FIG. 1 is a prospective view of the body controller of the present invention and affixed to a cylindrical housing carrying an instrument body, the controller being shown within the hand of a surgeon, or other human operator.

FIG. 2 is a lateral sectional view of the device as shown in FIG. 1

FIG. 3 is a view similar to that shown in FIG. 2, but illustrating the application of the thumb of the operator to the flexible means to manipulate the instrument body to expanded position.

FIG. 4 is a lateral sectional illustration of an alternate embodiment of the present invention.

FIG. 5 is a cross-sectional view taken along line 5—5 of FIG. 4.

DESCRIPTION OF THE PREFERRED EMBODIMENTS

Now with reference to FIG. 1, the endoscopic surgical instrument 10 of the present invention includes a body controller 100, a cylindrical housing 11 received through the frontal end of the body controller 100, and an instrument body 12 concentrically disposed within the cylindrical housing 11.

The body controller 100 is shown in FIG. 1 as being grasped in the fingers F1, F2, F3, and F4 and thumb T of the hand H of a surgeon or other human operator, with the thumb T being in contact with the housing portion 104 of a flexible means 105.

The housing 101 of the body controller 100 consists of a first section 102 for grasping by the fingers F1 through F4 of the human operator, and a second section or housing 104, which is designed for contact by the thumb T. The housing section 102 has an outer diameter 103 which is preferably smaller than the outer diameter 106 of the housing 104.

As shown in FIG. 1, the instrument 10 has an instrument body 12 shown in a second position 13, i.e., in relative expanded position.

The instrument body 12 may contain any one of a number of typical surgical instruments, such as a needle, scissors, probe, rake, or the like. For purposes of illustration only, the instrument body 12 is simply shown in the drawings as a section of cylindrical, or solid, conduit, which does not have affixed at its outer end any particular surgical instrument. Those skilled in the art will readily appreciate the fact that any one of a number of surgical instruments for use in endoscopic surgery may be affixed to or defined on the instrument body 12, and that the present invention is not limited to the incorporation or use of any particular endoscopic surgical device affixed to such end of the body 12.

FIG. 2 illustrates the instrument body 12 in the first, or retracted, position 14. As shown, the flexible means 105 houses a control means having a series of radially spaced laterally positioned ribs 107 thereon which are normally slightly flexed outwardly of the instrument body 12 within the interior of the flexible means 105. Each of the ribs 107 is flexed within the flexible means 105 by flexed engagement upon a shoulder 110 of a ring member 109 disposed exteriorly around the instrument body 12 approximate the frontal end of the flexible means 105, and by a companion flexing shoulder 108 on an inwardly extending protrusion portion of the first housing section 102.

The instrument body 12 securely receives therearound the ring 109 which, when the instrument 10 is activated, is permitted to move within a smooth inner wall 117 of the housing 101. An elastomeric seal member 111 is positioned frontal of the ring 109 within the housing 101 and around the instrument body 12 to prevent fluid communication between the instrument body 12 and the cylindrical housing 11 at the seal 111, to avoid escape of insufflation gases, and the like, during surgery.

A spring shoulder 113 extends within the first housing section 102 and has an opening 115 for receipt of the distal end of the instrument body 12. The distal end of the instrument body 12 has defined thereon an enlarged diameter spring stop 116 which shoulders against one end of a biased spring 112 housed around the exterior of the instrument body 12 between the stop 116 and a companion spring shoulder 113 on the ring element 114. Thus, as shown in FIG. 2, the instrument body 12 is in a relaxed or "normal" state or "normal position", whereby the instrument body 12 is in the first position 14, i.e., retracted, relative to the cylindrical housing 11.

When it is desired to activate the endoscopic surgical instrument 10, the housing 101 is grasped by the hand H of the operator, such that the fingers F1 through F4 lightly grasp the first section 102, with the inner face of the thumb T being lightly applied on the housing 104 of the flexible means 105.

As shown in FIG. 3, when it is desired to move the instrument body 12 from the first position 14 (FIG. 2) to the second position 13 (FIG. 1), the thumb T is lightly applied to the flexible means 105 to compress same such that the inner wall of the flexible means 105 contacts and engages a top surface of a rib 107, thus causing the ribs 107 to elongate. As the bias through the spring 112 is overcome by the elongation of the ribs 107 by further application of the force of the thumb T to the flexible means 105, the ring 109 will move laterally, frontally along the inner wall 117 to move the instrument body 12 concentrically within the cylindrical housing 111, until the body 12 is moved to the second position 13, as shown in FIG. 1.

When it is desired to move the instrument body 12 from a second position 13 to the first position or "normal" position 14, the application of slight pressure through the thumb T onto the flexible means 105 is reduced, and the spring bias in the spring 112 will move the ring 109 and the instrument body 12 within the inner wall 117 until the flexing ribs 107 are again expanded to the original or "normal" position within the interior of the flexible means 105, and, thus, the instrument body 12 is moved to the first position 14, as shown in FIG. 2.

Now with reference to FIG. 4, there is shown an alternate embodiment of the present invention. In this embodiment, the instrument body 12 is moved between first and second positions by rotating same, such that the first and second positions do not differ with respect to lateral alignment of the instrument body 12 and the cylindrical housing 11, but the instrument body 12 is rotated relative to the cylindrical housing 11. Such rotation may amount to only a few degrees, or may amount to full or partial circular rotation, and thus, any selective amount therebetween. As shown in FIG. 5, a disk 210 is secured around the instrument body 12 and, effectively replaces the ring 109 shown in the configuration of the instrument 10 in FIGS. 1, 2 and 3. The disk 210 has exteriorly defined therearound a series of outwardly protruding teeth 209, with valleys 209A disposed between each of the teeth 209. Each rib 207 has a collet 208 extending thereon with a collet finger 208A at the end of each collet for selective receipt within a respective valley 209A.

Thus, as shown in FIG. 4, as the thumb T is applied to the flexible means 105, the ribs 207 are lightly compressed to cause the biased collets to be moved from one valley 209A to another valley 209A and, in turn, cause rotation of the disk 210. As the disk 210 rotates, the instrument body 12, in turn, rotates a like degree corresponding to the degree of orientation between the respective valleys 209A.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the invention.

What is claimed and desired to be secured by Letters Patent is:

1. A hand-held surgical instrument comprising:
a housing having an open end and a longitudinal axis;
an instrument body disposed in the housing, the instrument body terminating in a working end, the instrument body and working end being movable relative to the housing between a first position and a second position;
a handle secured to the housing, the handle including a flexible portion located for engagement by an operator, said flexible portion overlying at least a portion of said instrument body; and
control means coupled between the handle and the instrument body and underlying the flexible portion for moving the instrument head between the first and second positions responsive to compression of the flexible portion by the operation in a direction substantially normal to the longitudinal axis of the housing.

2. The surgical instrument according to claim 1 wherein the control means includes at least one flexible rib coupled between the handle and the instrument body, wherein compression of the flexible portion deforms and elongates the rib to move the instrument body relative to the handle and housing.

3. The surgical instrument according to claim 1 wherein the flexible portion is an elastomeric member having a diameter larger than that of the housing.

4. The surgical instrument according to claim 1 wherein the instrument body moves axially in the housing and in the first position the working end is retracted in the housing and in the second position the working end extends beyond the open end of the housing.

5. The surgical instrument according to claim 4 further comprising a biasing member coupled between the handle and instrument body to urge the working end of the instrument body into the first position.

6. A hand-held surgical instrument comprising:
a housing having an open end;
an instrument body disposed in the housing and axially moveable relative to the housing, the instrument body terminating in a working end, the working end normally being in a retracted position within the housing;

a handle secured to the housing, the handle including a flexible portion located for engagement by an operator; and at least one flexible rib coupled between the handle and the instrument body, wherein compression of the flexible portion deforms and elongates the rib to move the instrument body relative to the housing, wherein the working end extends beyond the open end of the housing.

7. The surgical instrument according to claim 6 wherein the flexible portion is an elastomeric member having a diameter larger than that of the housing.

8. The surgical instrument according to claim 6 further comprising a biasing member coupled between the handle and instrument body to urge the working end of the instrument body into the retracted position.

* * * * *